(12) United States Patent  
Goodley

(10) Patent No.: US 7,462,280 B2
(45) Date of Patent: Dec. 9, 2008

(54) LIQUID CHROMATOGRAPHY CHIP WITH FLEXIBLE INTERFACE

(75) Inventor: Paul C. Goodley, Cupertino, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 621 days.

(21) Appl. No.: 11/187,084

(22) Filed: Jul. 22, 2005

(65) Prior Publication Data

US 2007/0017869 A1 Jan. 25, 2007

(51) Int. Cl.
*B01D 15/08* (2006.01)

(52) U.S. Cl. ............... 210/198.2; 210/656; 422/100; 422/104

(58) Field of Classification Search ............ 210/101, 210/143, 198.2, 656; 95/82; 96/101; 422/100, 422/104
See application file for complete search history.

(56) References Cited

U.S. PATENT DOCUMENTS

| | | | |
|---|---|---|---|
| 5,132,012 A * | 7/1992 | Miura et al. ............... | 210/198.2 |
| 5,658,413 A * | 8/1997 | Kaltenbach et al. ...... | 156/272.8 |
| 5,792,943 A * | 8/1998 | Craig ....................... | 73/61.52 |
| RE36,350 E * | 10/1999 | Swedberg et al. ........ | 210/198.2 |
| 6,033,628 A * | 3/2000 | Kaltenbach et al. ........ | 422/68.1 |
| 6,264,892 B1 | 7/2001 | Kaltenbach et al. | |
| 6,318,157 B1 | 11/2001 | Corso et al. | |
| 6,548,263 B1 | 4/2003 | Kapur et al. | |
| 6,576,896 B2 | 6/2003 | Figeys et al. | |
| 6,812,458 B2 | 11/2004 | Gregori et al. | |
| 6,845,968 B2 * | 1/2005 | Killeen et al. ............... | 251/304 |
| 6,958,119 B2 * | 10/2005 | Yin et al. .................. | 210/198.2 |
| 2002/0100714 A1 * | 8/2002 | Staats ......................... | 210/85 |
| 2003/0015682 A1 * | 1/2003 | Killeen et al. ............... | 251/368 |
| 2003/0017609 A1 * | 1/2003 | Yin et al. ..................... | 436/161 |
| 2003/0116206 A1 * | 6/2003 | Hartshorne et al. .... | 137/625.46 |
| 2006/0222571 A1 * | 10/2006 | Baeuerle et al. ............. | 422/103 |
| 2007/0025887 A1 * | 2/2007 | Baeuerle et al. ............. | 422/104 |

* cited by examiner

*Primary Examiner*—Ernest G Therkorn

(57) ABSTRACT

A liquid chromatography chip may include an analytical column. After an analyte has traveled through an analytical column defined by the chromatography chip, the analyte is routed, either directly or indirectly, to a port defined by the chromatogrpahy chip, instead of to a spray tip on-board the chromatography chip. The port may be in fluid communication with a tube or conduit that may, in turn, be coupled to another device. Such an arrangement provides for flexible interface of the chromatography chip to another device.

7 Claims, 9 Drawing Sheets

LIQUID CHROMATOGRAPHY CHIP WITH FLEXIBLE INTERFACE

BACKGROUND

Liquid chromatography is a process by which a substance may be separated into its constituent ions or molecules. Typically, the substance is dissolved in a solvent and is driven through an analytical column by a pump. The analytical column is filled with a packing material known as a "stationary phase." The various components of the solution pass through the stationary phase at different rates, due to their interaction with the stationary phase.

Liquid chromatography may be used as an initial phase prior to further analysis via a mass spectrometer. Per such an arrangement, a substance to be analyzed is first separated into its constituents by a liquid chromatograph. Thereafter, time-sequenced samples are delivered from the output of the liquid chromatograph to the input of the mass spectrometer, i.e., into the ion source of the mass spectrometer.

In instances in which the mass spectrometer utilizes electrospray ionization, it is known to embody the liquid chromatograph as a small polymeric chip. In other words, the analytical column exists as a channel (packed with a treated stationary phase material) extending through the body of the chip. The output of the packed channel is connected to a second channel that extends to distal region of the chip, which is fashioned as a spray tip. The spray tip portion of the chip is inserted into the ion source of the mass spectrometer. Thus, the substance to be analyzed is separated into its constituents by the packed column embodied on the chip, and is then delivered, via the spray tip, into the mass spectrometer for further analysis.

The above-described scheme exhibits certain characteristics. To properly interface the chromatography chip with the ion source of the mass spectrometer, the spray tip region of the chip must be precisely shaped to mate with the ion source. Additionally, the chip must be precisely oriented relative to the mass spectrometer. Thus, the chromatography chip must be designed in light of the specific mass spectrometer to which it is to be mated, meaning that it cannot effectively function as a stand-alone unit.

SUMMARY

In general terms, the present invention is directed to a chromatography chip that routes an analyte to a port defined by the chromatography chip, rather than to a spray tip onboard the chromatography chip.

According to one embodiment, a liquid chromatography device may include a chip having a body with a first surface and an oppositely disposed second surface. The body may define a first channel having an input end and an output end. Also, the first channel may contain a chemically treated material. The second surface of the chip body may define a first void that is in fluid communication with the input end of the first channel. The body may define a second channel in fluid communication with the output end of the first channel. The second channel may be in fluid communication with a second void defined by the second surface of the chip body.

According to another embodiment, a liquid chromatography system includes a chip having a body with a first surface and an oppositely disposed second surface. The body defines a first channel having an input end and an output end. The first channel contains a chemically treated material. The first channel is in fluid communication with a first void defined by the second surface of the chip body. The system also includes a stator coupled to the first surface of the chip. Additionally, the system includes a rotor having a chip-side surface coupled to the second surface of the chip. The chip-side surface of the rotor has a groove thereon. Still further the system may include an actuator coupled to the rotor and arranged to rotate the rotor so that, at some point in the rotation of the rotor, the groove on the rotor comes into fluid communication with the first void on the second surface of the chip.

According to yet another embodiment, a method of liquid chromatography includes pumping a mobile phase fluid carrying an analyte to one of a plurality of channels extending through a stator. The method also includes receiving the mobile phase fluid carrying the analyte in one of a plurality of channels defined by a chip. Still further, the method includes driving the mobile phase fluid through a path extending through at least one channel defined by the chip. The at least one channel contains a chemically treated material. Thus, an effluent is yielded from the at least one channel. The composition of the effluent varies with time. Finally, the effluent is delivered to a tube.

DETAILED DESCRIPTION

Figures 1A, 1B:
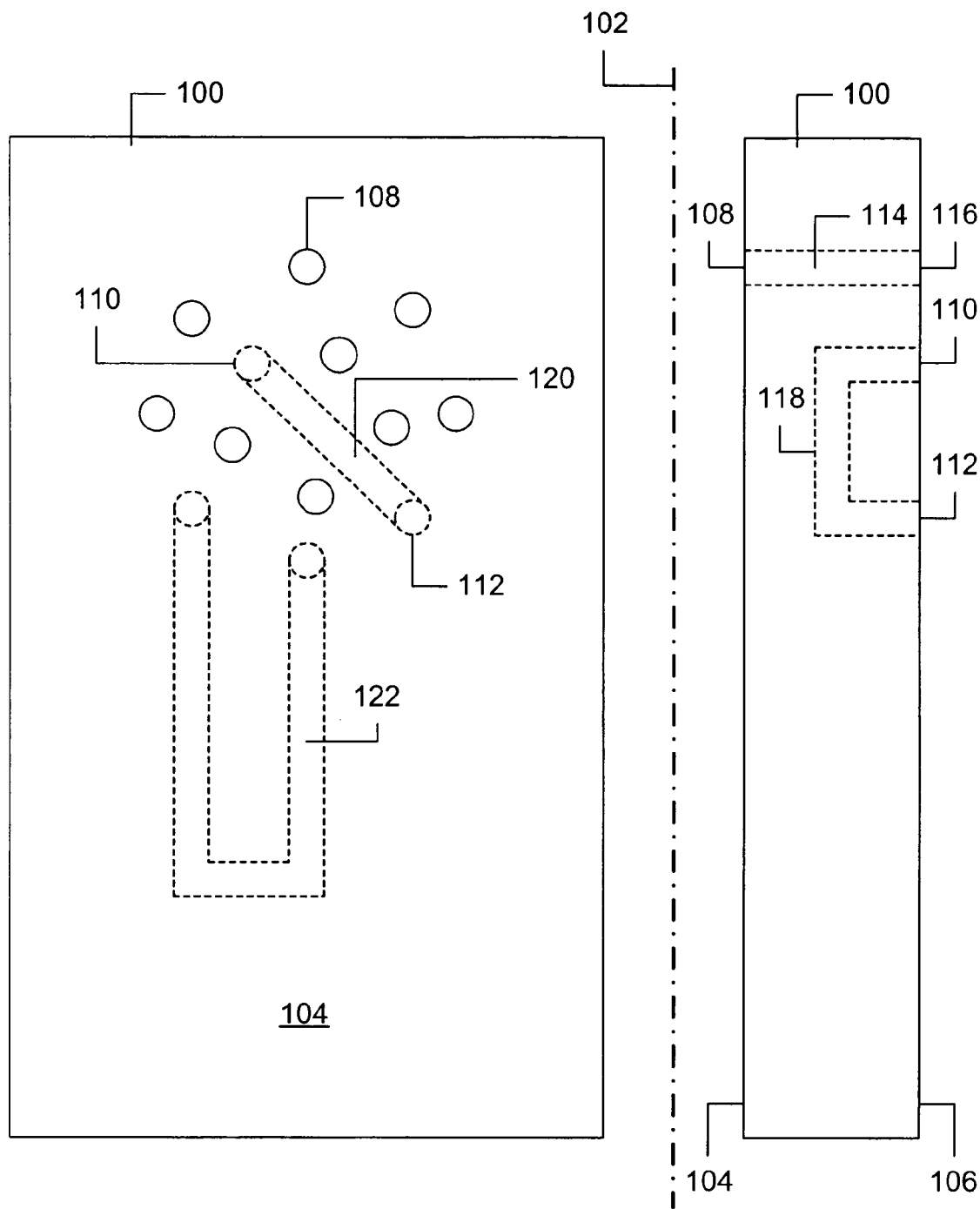
FIG. 1A depicts a stator-side view of one possible embodiment of a chromatography chip.
FIG. 1B depicts a simplified side-view of the chromatography chip of FIG. 1A.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

FIG. 1A depicts an embodiment of a liquid chromatography device 100. A simplified, partial side view of the liquid chromatography device, projected across line 102, is presented in FIG. 1B. For the sake of simplicity, only the channels extending between ports identified by reference numerals in FIG. 1A are depicted in FIG. 1B. The chromatography device 100 is embodied as a thin wafer or chip, and is referred to herein as a "chromatography chip."

In the exemplary embodiment, the chromatography chip 100 is polymeric, although it could be made from other materials. For example, the chromatography chip may be fabricated from polyimide, amongst other possibilities. The chromatography chip 100 has an upper surface 104, which is shown in FIG. 1A, and an opposed lower surface 106, which is not visible in FIG. 1A, but is depicted in FIG. 1B. The upper and lower surfaces 104 and 106 are depicted as being rectangular. In principle, the shape of the upper and lower surfaces 104 and 106 is a matter of design choice, and may take on any form.

In the exemplary embodiment, the chromatography chip 100 is thin. For example, according to one embodiment, the chromatography chip 100 is about 30 mils thick (i.e., the upper and lower surfaces 104 and 106 are separated from one another by 30 mils), and may be embodied as multiple stacked chromatography chips. According to another embodiment, the chromatography chip is about one inch in width, and is about two to about six inches in length. The aforementioned dimensions of the chromatography chip are the subjects of design choice. Therefore, various embodiments of the chromatography chip may be wider and/or longer, depending whether a stacked embodiment is used, or whether the chip includes multiple sample processing channels, etc.

The figures presented herein, including FIGS. 1A and 1B, are not drawn to scale. For the sake of illustration, certain features that would otherwise be quite small have been depicted as exaggeratedly large. For example, the thickness of the chromatography chip 100 has been exaggerated, in order to provide a better view of certain features of the chromatography chip 100. The size of other features has also been distorted, for similar reasons.

The upper surface 104 of the chromatography chip 100 defines a set of holes or ports, one of which is identified by reference numeral 108. The lower surface 106 of the chip also defines a set of ports, two of which are identified by reference numerals 110 and 112. In FIG. 1A, ports that are defined by the upper surface 104 (e.g., port 108) are depicted with a solid line. On the other hand, ports that are defined by the lower surface 106 (e.g., ports 110 and 112) are depicted with a dashed line.

A port is a void defined by a surface 104 or 106 of the chromatography chip 100. According to one embodiment, the ports are about two microns in diameter. Of course, the aforementioned diameter is a matter of design choice, and may therefore vary, as is understood in the art. Each port provides access to a channel. For example, in the case of port 108, access is provided to channel 114, which extends from the upper surface 104 to the lower surface 106, terminating at port 116 defined in the lower surface 106 of the chip 100. Therefore, a device, such as a tube or conduit, in fluid communication with port 108 is also in fluid communication with port 116 by virtue of the channel 114 that extends between them. Turning to another example, in the case of port 110, access is provided to channel 118, which runs along a tripartite path: (1) beginning at port 110 and extending towards the upper surface 104; (2) extending through the chip body 100, in a partially width-wise and partially length-wise direction; and (3) extending again toward the lower surface, and terminating at port 112. Thus, a device in fluid communication with port 110 is also in fluid communication with port 112 by virtue of the channel 118.

Each channel may be terminated by two ports. A channel may be terminated by two ports defined by the same surface (i.e., both ports are on the lower surface 106, or both ports are on the upper surface 104), in which case the channel extends length-wise and/or width-wise through the body of the chip before returning to the surface from which it originated. Alternatively, a channel may be terminated by ports on opposed surfaces. For example, such a channel may extend along the z-axis of the chip 100, directly coupling the oppositely opposed ports, as shown by channel 114. On the other hand, such a channel may extend length-wise and/or width-wise through the body of the chip before extending to a port on the opposite surface. In some exemplary embodiments of a chromatography chip, one or more channels may be linear. In other embodiments, one or more channels may be non-linear.

Figure 2A:
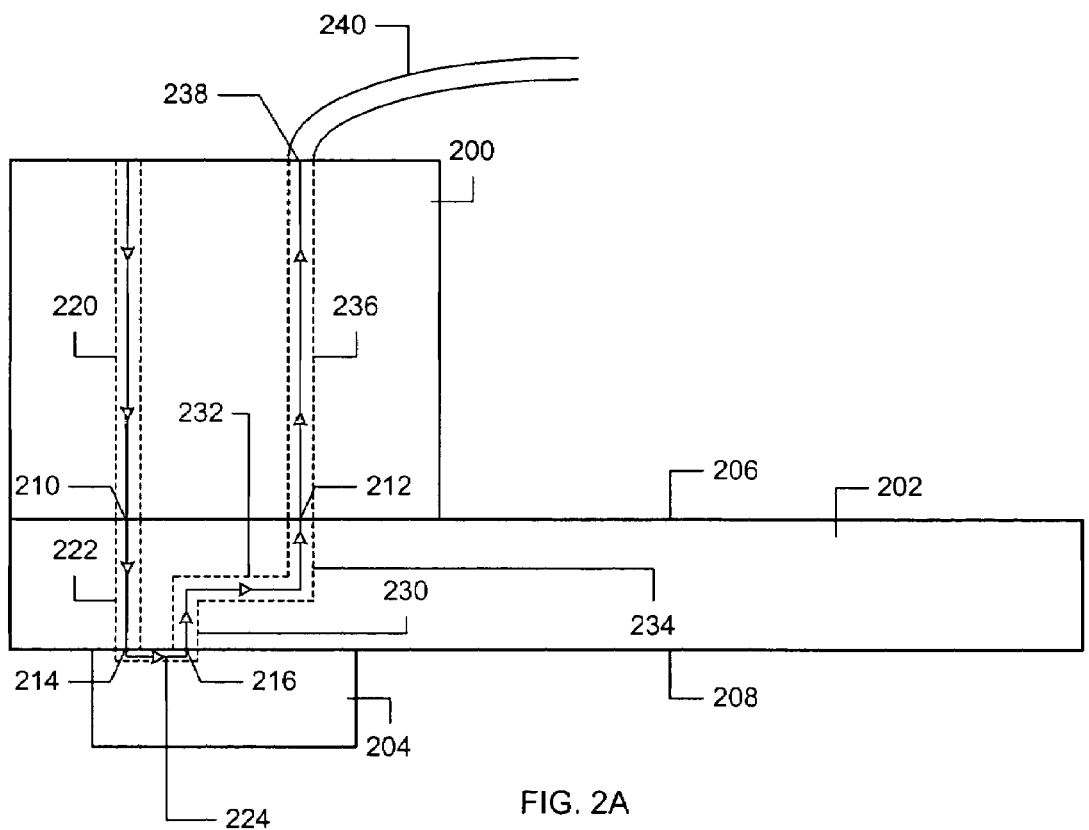
FIG. 2A depicts a side-view of one possible embodiment of a chromatography system.
Figure 2B:
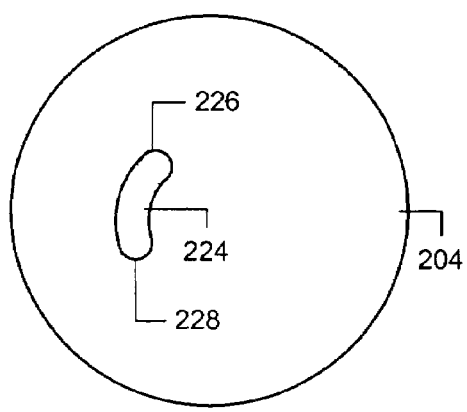
FIG. 2B depicts a rotor that, according to one possible embodiment, may be an element of the system depicted in FIG. 2B.

A chromatography chip, such as the one depicted in FIGS. 1A and 1B may be used in connection with a system, such as that depicted in FIGS. 2A and 2B. The system includes a stator 200, a chromatography chip 202, and a rotor 204.

In FIG. 2A, the exemplary embodiment of the chromatography chip 202 is depicted from a side view, with its upper surface 206 abutting the stator 200, and its lower surface 208 abutting the rotor 204. Hence, the upper surface of the chromatography chip 202 may be referred to herein as the "stator-side surface," and the lower surface 208 may be referred to herein as the "rotor-side surface."

The chromatography chip depicted in FIG. 2A contains two ports 210 and 212 on the upper surface 206, and two ports 214 and 216 on the lower surface 208. A practical commercial embodiment of a chromatography chip may contain many more ports, as discussed below. The chromatography chip 202 presented in FIG. 2A is simplified for the sake illustrating the combined functionality of the stator 200, chromatography chip 202, and rotor 204.

The stator 200 couples to the upper surface of the chip 206, and functions as an input manifold. A fluid to be introduced into port 210 on the upper surface 206 of the chromatography chip 202 may be injected into port 218 of the stator 200. The fluid then travels through a channel 220 extending length-wise through the stator 200, and arrives at port 210. Upon reaching port 210, the fluid travels through channel 222, and arrives at port 214 on the lower surface 208 of the chromatography chip 202.

The rotor 204 serves the purpose of selectively providing fluid communication between ports on the lower surface 208 of the chromatography chip 202. A view of the chip-side surface of the rotor 204 is presented in FIG. 2B. As can be seen in FIG. 2B, the rotor 204 includes a groove 224 etched into the surface of the chromatography chip. According to one embodiment, the groove 224 may be on the order of 0.001 inches deep. Although not depicted in FIG. 2B, the rotor 204 may be rotated by an actuation device, such as a servomotor, for example. Rotation of the rotor 204 causes concomitant rotation of the groove 224. By rotating the rotor 204 to a defined angle, the groove 224 may be oriented so that one extremity 226 of the groove 224 aligns with port 214, and another extremity 228 aligns with port 216. When thus positioned, the groove 224 provides fluid communication between the ports 214 and 216. Rotation of the rotor 204 to another angle may cause port 214 to come into fluid communication with another port on the lower surface 208 of the chromatography chip 202, or may cause port 214 to be terminated (i.e., not in fluid communication with any other port).

As depicted in FIG. 2A, the groove 224 is oriented so that fluid communication is provided between ports 214 and 216. Therefore, fluid reaching port 214 travels through the groove 224, and is reintroduced into the chromatography chip at port 216. Thereafter, the fluid travels through the channel 230, and is communicated to channel 232, which extends length-wise through the chromatography chip body 202. Channel 232 may be packed with packing material, such as silica beads, for example, causing the channel 232 to function as an analytical column. Thus, fluid reaching channel 232 is separated into its constituent molecules, which are communicated via channel 234 to port 212 as a function of time. Thereafter, the column 232 effluent exits the system by way of stator channel 236, reaching an output port 238 on the upper surface of the stator 200.

A tube or conduit 240 may be connected to port 238. According to one embodiment, the tube 240 may be fashioned as a fused silica conduit or other appropriate conduit, having an inner diameter on the order of approximately 2-1000 micrometers. The aforementioned diameter of the tubing 240 is a design choice governed by other factors and may therefore vary, as is understood in the art. The tube 240 may provide fluid communication to any desired device. For example, the tube 240 may provide fluid communication with a spray tip that is embedded in the ion source of a mass spectrometer, or to other devices, such as fraction collectors, matrix-assisted laser desorption (MALDI) plates, ultraviolet cells, etc. Accordingly, the chromatography chip depicted in FIG. 2A (an in the other figures herein) does not include a spray tip. Thus, the system shown in FIG. 2A functions as a stand-alone chromatography unit that may be coupled, via the tube 240 to any desired device. Such device may include, without limitation, a mass spectrometer, an ultraviolet cell, a fraction collector or a MALDI plate, etc.

Returning to FIG. 1A, certain features of the chromatography chip 100 are of note, but not essential. As shown therein, the chromatography chip 100 includes a trapping column 120 and an analytical column 122. As described below, the chromatography chip 100 may be mated with a rotor, so that an analyte carried by a fluid is trapped at the head of the trapping column, and is desalted. Thereafter, the rotor may be rotated, so as to cause the analyte to pass through the trapping column 120, and enter the analytical column 122, whereupon the analyte is separated into its constituents, which exit the analytical column 122 as a function of time. Thereafter, the column effluent is directed to a port in communication with the stator, whereupon it is directed via a tube to to a desired device, as described previously.

To permit the aforementioned operation to occur with simple rotation of a rotor, the ports on the lower surface 106 (i.e., rotor-side surface) of the chromatography chip 100 may be arranged along one or more concentric circular paths, as shown in FIG. 1A. Thus, as shown in FIG. 1A, the ports on the lower surface 106 of the chromatography chip 100 are arranged along two concentric circular paths.

Figure 3:
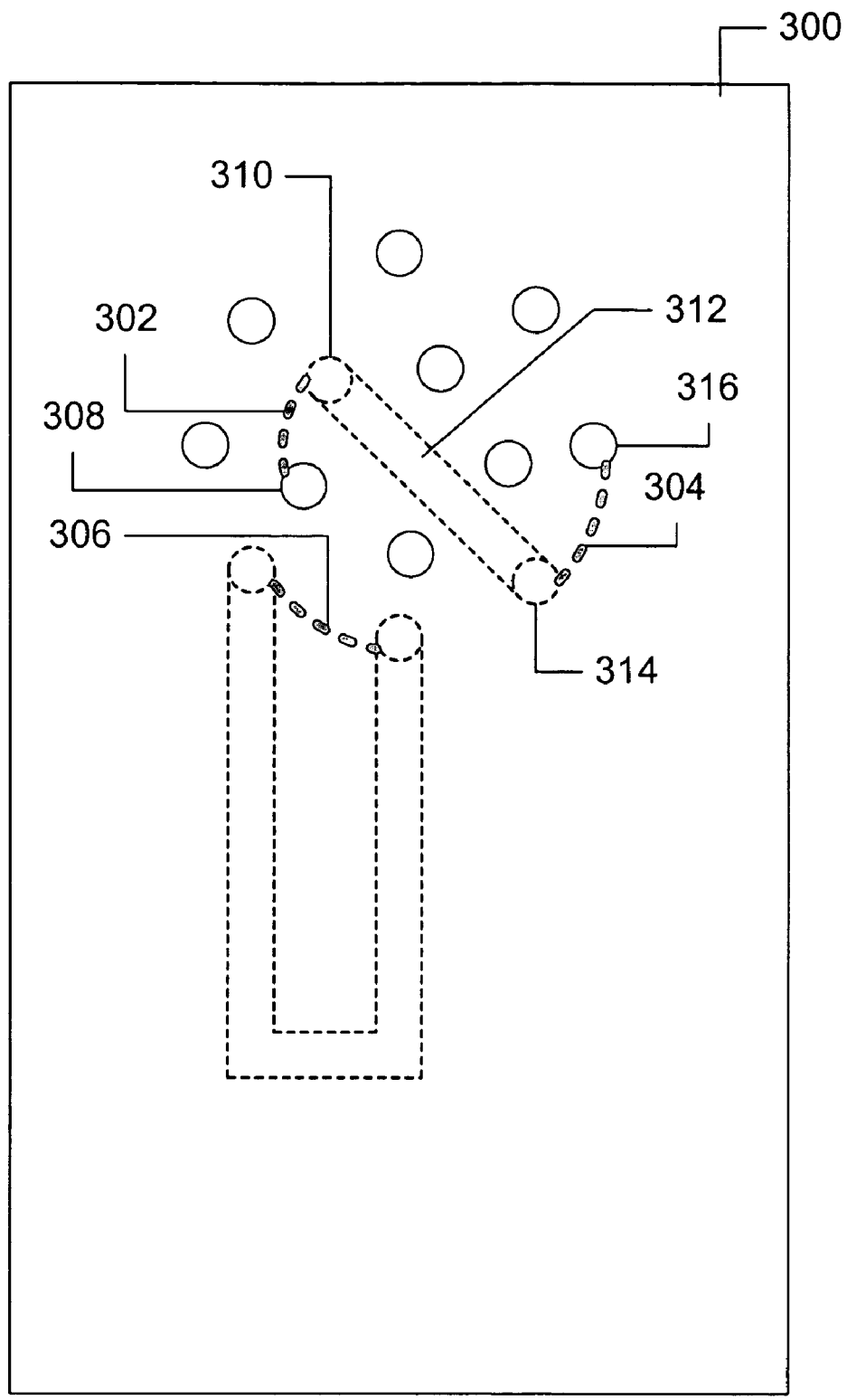
FIG. 3 depicts a stator-side view of one possible embodiment of a chromatography chip.
Figure 4:
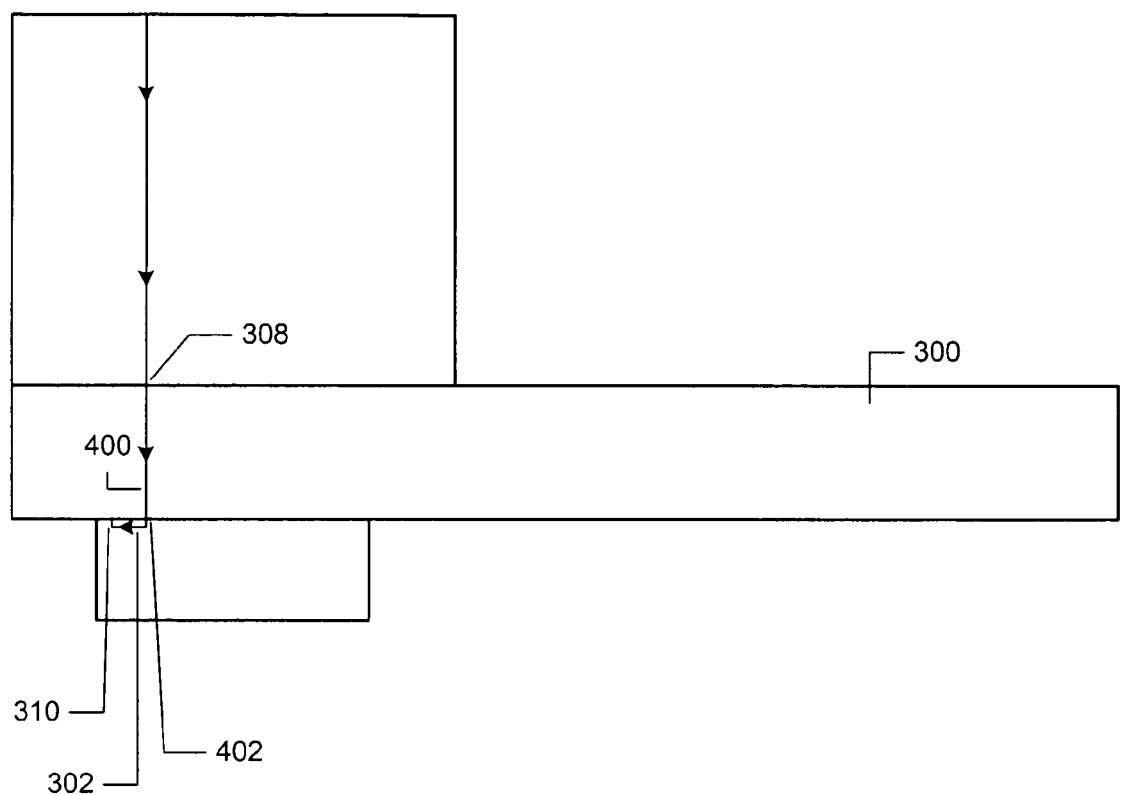
FIG. 4 depicts a portion of a path through which a fluid runs during one possible embodiment of a desalting process.
Figure 5:
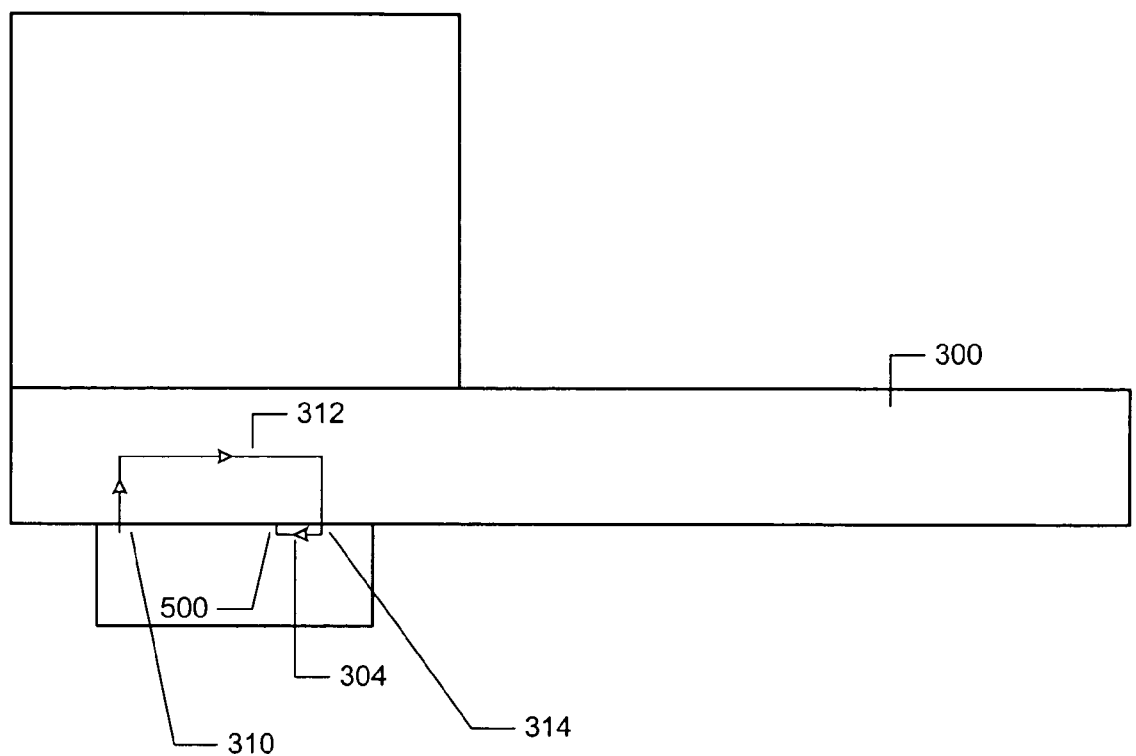
FIG. 5 depicts another portion of a path through which a fluid runs during one possible embodiment of a desalting process.
Figure 6:
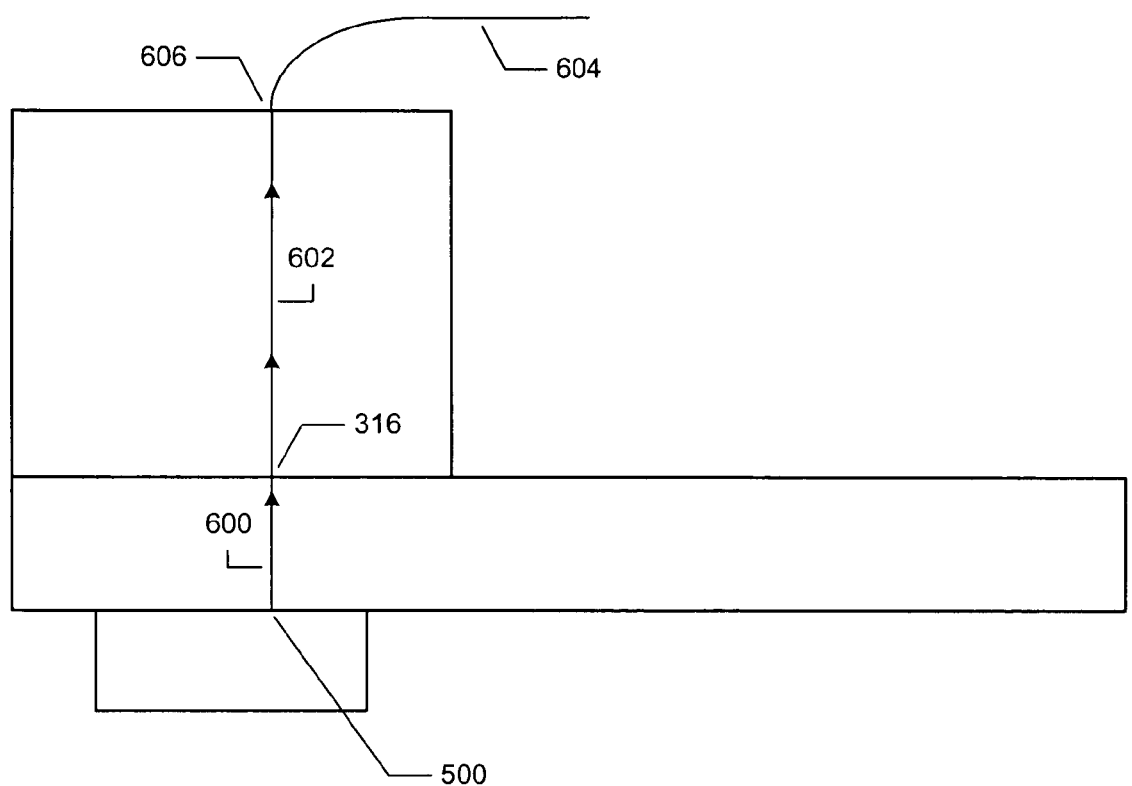
FIG. 6 depicts yet another portion of a path through which a fluid runs during one possible embodiment of a desalting process.

Also of note in FIG. 3, is that the chromatography chip 300 possesses a plurality of ports that lead neither to a trapping column, nor to an analytical column. The provision of such ports permits the combination of the stator, rotor, and chromatography chip to cooperatively function as a switching device that directs fluid from one unit of equipment to another, for example. Alternatively, such ports may be used to provide a mechanism by which multiple pumps may coupled to the columns therein.

FIG. 3 depicts an exemplary chromatography chip 300 (view of top surface) arranged to initially desalt and then separate an analyte. The discussion related to FIG. 3-9 is one example in which a stator, rotor, and chromatography chip cooperatively function so as to initially couple one pump to a given column, and to subsequently couple a different pump to that column. The depiction of FIG. 3 includes three heavy dashed lines 302, 304, and 306. These heavy dashed lines represent fluid pathways (or grooves) provided by a rotor, which abuts the lower surface of the chromatography chip 306, and is therefore not visible in FIG. 3. Given the orientation of the rotor in FIG. 3, an analyte delivered to the chip 300 undergoes a desalting process or washing, as described below.

Initially, a fluid carrying an analyte is propelled by force of a pump, such as a capillary pump, through an input port on a stator, which is in fluid communication with port 308 on the upper surface of the chromatography chip 300. (For the sake of illustration, the fluid carrying the analyte is assumed to be water. Of course, other fluids may be used, as is understood by those of skill in the art.) A capillary pump is a variety of pump that exhibits a flow rate on the order of picoliters/min to microliters/min. The fluid flows through the port 308, and traverses a channel 400 coupled thereto (see FIG. 4), reaching a port 402 on the lower surface of the chromatography chip 300. A groove 302 provides fluid communication between port 402 and port 310, and therefore the fluid travels to port 310.

Port 310 is in fluid communication with channel 312, which is packed with a hydrophobic packing material or other material(s) required for the method used in the chemical process. Accordingly, the water passes through the column 312, while the analyte remains at the head of the column. For this reason channel 312 is referred to as a "trapping column" (the analyte remains "trapped" at the head of the column). As the water passes through the column 312, it carries away contaminant salts that may be commingled with the analyte, a process known as "desalting." The water and salts dissolved therein constitute a waste fluid that is carried to port 314 on the lower surface of the chromatography chip 300, leaving the adsorbed hydrophobic material on the trapping column.

Groove 304 provides fluid communication between port 314 and port 500 (FIG. 5) on the lower surface of the chromatography chip 300. Therefore, the waste fluid flows from port 314 to port 500. A channel 600 (FIG. 6) couples port 500 on the lower surface of the chip 300 to port 316 on the upper surface of the chromatography chip 300, and the waste fluid therefore exits the chip 300 by way of port 316, and enters a channel 602 that extends through the stator. A tube or conduit 604 is coupled to the stator at port 606. Therefore, the waste fluid is removed from the stator via the tube 604, and carried to a waste fluid receptacle (not depicted).

The previously described desalting process may continue for several minutes, until the analyte is determined to be sufficiently purified or deslated. Thereafter, the rotor may be rotated in the clockwise direction, causing the grooves to form the couplings depicted in FIG. 7.

Figure 7:
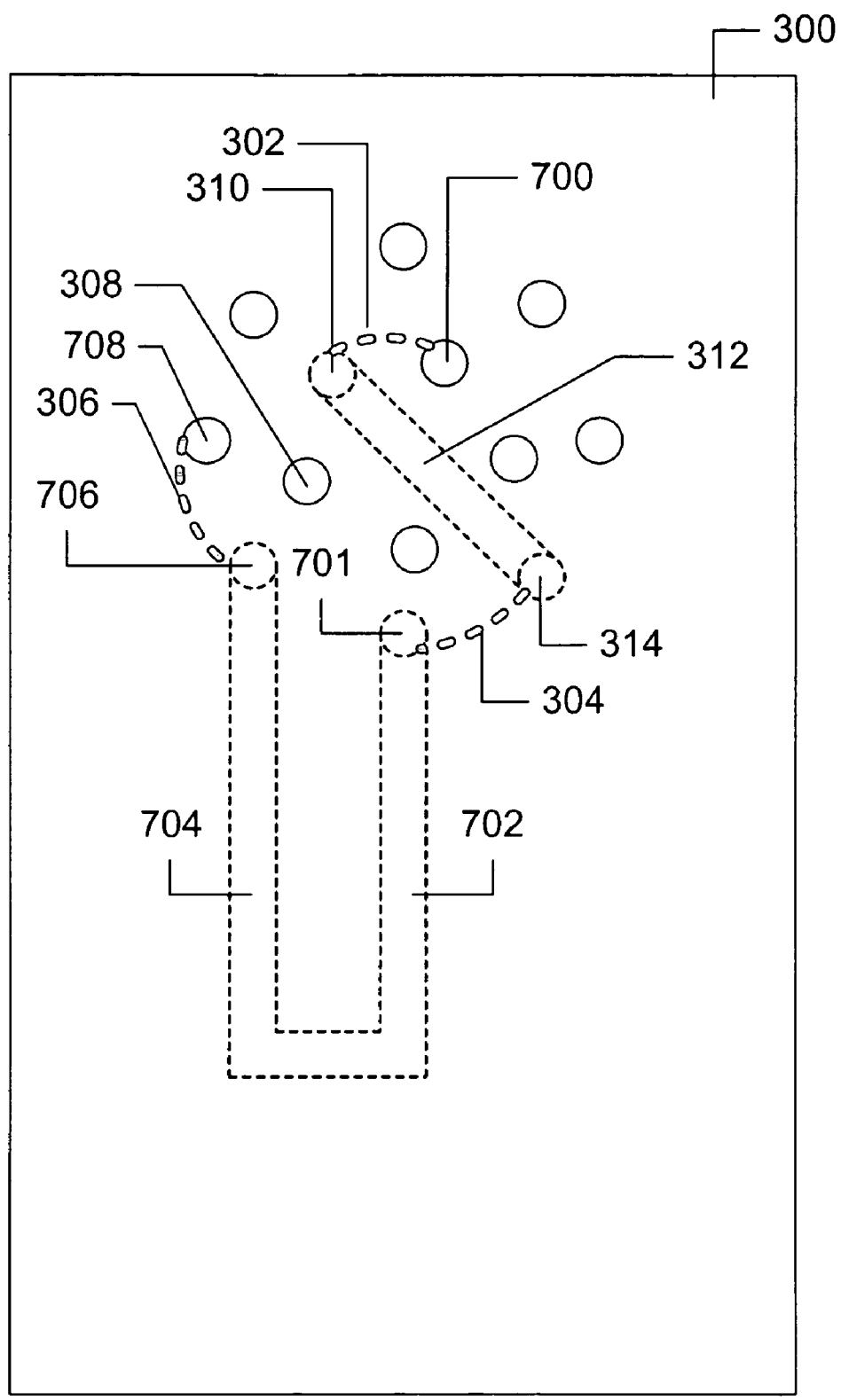
FIG. 7 depicts a stator-side view of one possible embodiment of a chromatography chip.
Figure 8:
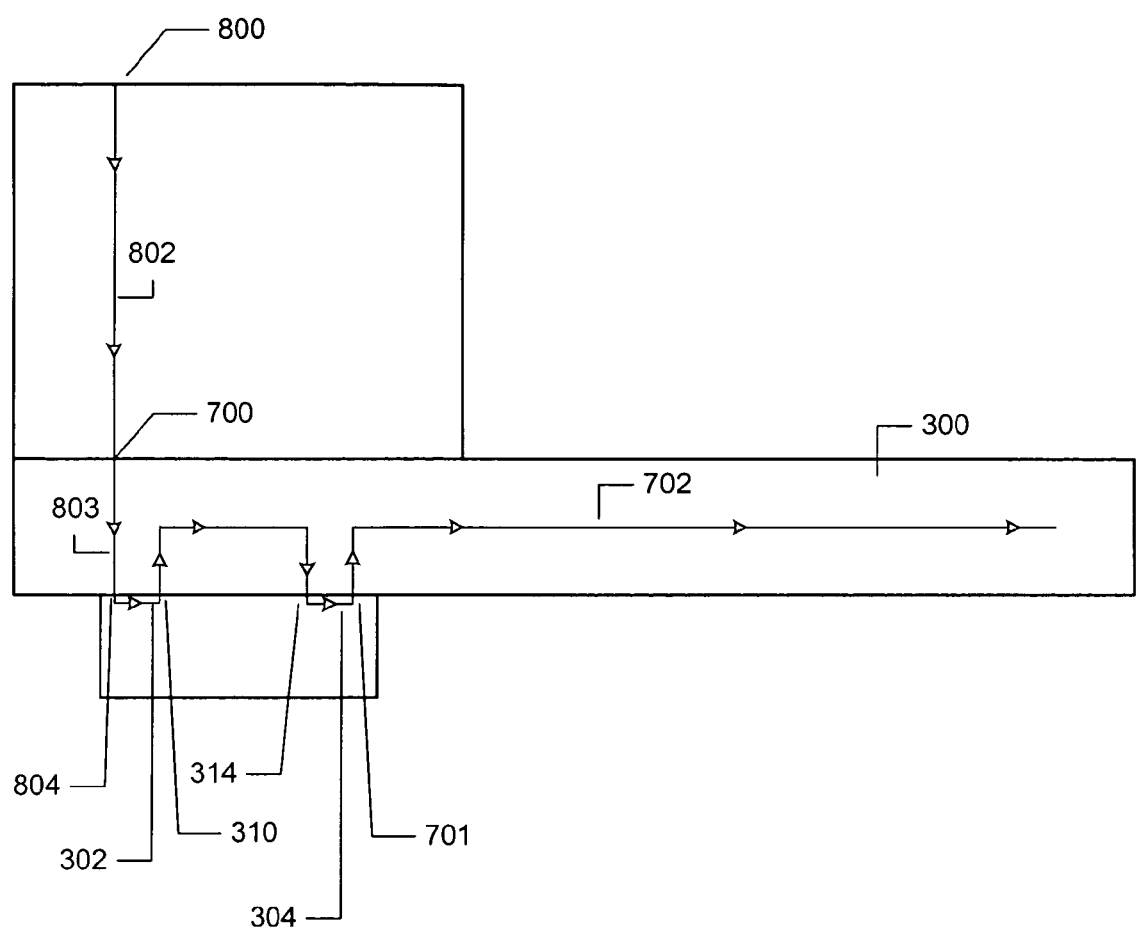
FIG. 8 depicts a portion of a path through which a fluid runs during one possible embodiment of a chromatography process.

As can be seen from FIG. 7, port 308 is no longer in fluid communication with port 310. Instead, port 700 is in fluid communication with port 310. As shown in FIG. 8, port 700 is in fluid communication with port 800 of the stator (via channel 802). A pump, such as a nanopump, may drive a hydrophilic fluid, such as acetonitrile, through the port 800, and therefore through channel 802, meaning that the hydrophilic fluid enters the chromatography chip 300 by way of port 700. A nanopump is a variety of pump that exhibits a flow rate on the order of microliters to low nanoliters per minute. A channel 803 couples port 700 to port 804 on the lower surface of the chip. Accordingly, the hydrophilic fluid exits the chip 300 by way of port 804.

Groove 302 provides fluid communication between port 804 and port 310. Therefore, the hydrophilic fluid re-enters the chip at port 310. Upon re-entry of the hydrophilic fluid, it passes through the head of the trapping column 312, thereby dissolving the hydrophobic analyte and carrying it through the trapping column 312, whereupon the column effluent exits the chromatography chip by way of port 314 at the lower surface of the chip 300.

By virtue of the orientation of the rotor, groove 304 provides fluid communication with port 701. Thus, the effluent re-enters the chip 300 by way of port 701, and flows through channel 702. Channel 702 is packed with a packing material such as silica treated beads, thereby separating the effluent-analyte solution into its consituent molecules, which exit the column 702 with a composition that is a function of time.

Figure 9:
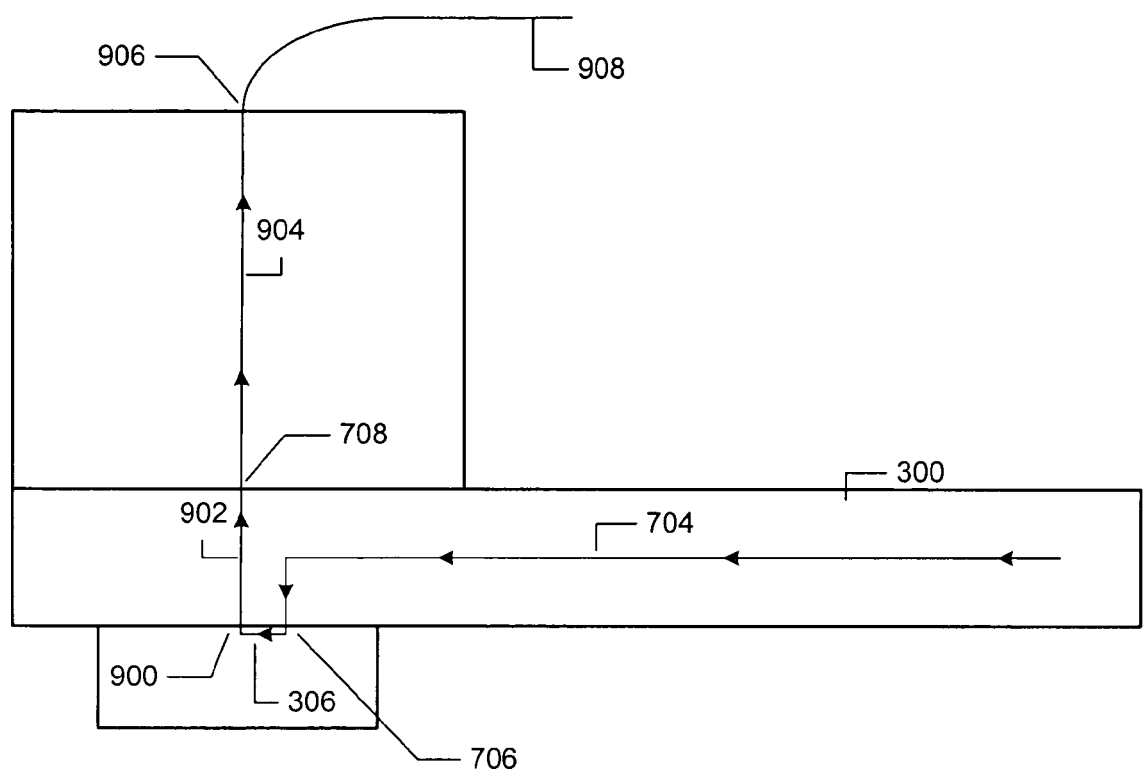
FIG. 9 depicts a portion of a path through which a fluid runs during one possible embodiment of a chromatography process.

Alternately referring to FIG. 9 and FIG. 7, upon exit from the analytical column 702, the column effluent traverses channel 704, and exits the chip 300 by way of port 706. Groove 306 on the rotor provides fluid communication between port 706 and port 900 on the lower surface of the chromatography chip. Accordingly, the effluent re-enters the chromatography chip 300 at port 900, and flows through channel 902, exiting the chromatography chip at port 708 on the upper surface of the chromatography chip 300.

Upon exiting the chromatography chip, the effluent travels to output port 906 on the stator, by way of channel 904. Thereafter, the effluent is carried to by way of a tube or conduit to a device coupled thereto, such as a spray tip embedded in an ion source of a mass spectrometer or other anayltical devices, including MALDI plates, etc.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

Furthermore, in the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims.

The invention claimed is:

1. A liquid chromatography system comprising:
   a chip having a body with a first surface and an oppositely disposed second surface, wherein the body defines a first channel having an input end and an output end, the first channel containing a chemically treated material, and wherein the first channel is in fluid communication with a first void defined by the second surface of the chip body;
   a stator coupled to the first surface of the chip;
   a rotor having a chip-side surface coupled to the second surface of the chip, the chip-side surface having a groove thereon;
   an actuator coupled to the rotor and arranged to rotate the rotor so that, at some point in the rotation of the rotor, the groove on the rotor comes into fluid communication with the first void on the second surface of the chip.

2. The system of claim 1, wherein the chip body defines a second channel extending between a second void defined by the second surface of the chip and a third void defined by the first surface of the chip, and wherein the groove on the rotor is arranged so that, at some point during the rotation of the rotor, the groove creates fluid communication between the first and second voids on the second surface of the chip.

3. The system of claim 2, wherein the stator defines a void extending through the stator, wherein the void extending through the stator is in fluid communication with the third void on the first surface of the chip.

4. The system of claim 3, further comprising a tube coupled to the void extending through the stator.

5. The system of claim 4, wherein the tube joins the chip to a mass spectrometer.

6. The system of claim 1, wherein the chip body does not include a spray tip.

7. The system of claim 1, wherein the first surface of the chip defines a plurality of voids.

* * * * *